United States Patent [19]

Yamamoto et al.

[11] Patent Number: 5,336,779
[45] Date of Patent: Aug. 9, 1994

[54] METHOD OF PRODUCING FORMYLIMIDAZOLES

[75] Inventors: Toshio Yamamoto, Ogaki; Kazumasa Hirata, Osaka; Shigenori Wakabayashi, Osaka; Akio Katsuura, Osaka, all of Japan

[73] Assignee: Nippon Gohsei Kagaku Kogyo Kabushiki Kaisha, Osaka, Japan

[21] Appl. No.: 125,220

[22] Filed: Sep. 23, 1993

[30] Foreign Application Priority Data

Oct. 8, 1992 [JP] Japan .................. 4-297705
Feb. 16, 1993 [JP] Japan .................. 5-51515
Feb. 16, 1993 [JP] Japan .................. 5-51516

[51] Int. Cl.$^5$ .......................... C07D 233/64
[52] U.S. Cl. .................. 548/333.5; 568/431; 568/471
[58] Field of Search ......... 548/333.5; 568/431, 568/471

[56] References Cited

U.S. PATENT DOCUMENTS 3,692,840 9/1972 Frangatos .................. 568/431
4,107,308 8/1978 Paul et al. .................. 424/249

FOREIGN PATENT DOCUMENTS 0514198 11/1992 European Pat. Off. .

OTHER PUBLICATIONS

CA 116(25):255614j Preparation . . . Derivatives, Kakimoto, p. 792, 1992.
The Chemistry of the Carbonyl Group, Ed. Saul Patai & Zvi Rappaport, Palladium and Platinum, pp. 134–136, Verter, 1970.

Primary Examiner—Joseph Paul Brust
Assistant Examiner—Joseph K. McKane
Attorney, Agent, or Firm—Armstrong, Westerman, Hattori, McLeland & Naughton

[57] ABSTRACT

In producing formylimidazoles by catalytically oxidizing the corresponding 4- or 5-hydroxymethylimidazoles, the catalytic oxidation is carried out in the presence of a noble metal catalyst while oxygen or air is blown into the reaction system. In this case, it is particularly desirable that the catalytic oxidation in the presence of a noble metal catalyst be carried out in a solvent comprising an aqueous alkali or in a mixed solvent composed of an aqueous alkali and an organic solvent immiscible with water.

5 Claims, No Drawings

METHOD OF PRODUCING FORMYLIMIDAZOLES

FIELD OF THE INVENTION

The present invention relates to a method of producing formylimidazoles which are useful as raw materials for the production of drugs, for example diuretics and antihypertensive agents.

BACKGROUND OF THE INVENTION

4-Formylimidazoles and 5-formylimidazoles are useful as raw materials for the production of drugs, for example diuretics and antihypertensive agents, and are chemicals attracting attention in recent years.

As for the production of these formylimidazoles, only a very few references can be cited. The only production methods so far studied comprise using 2-alkyl-5-hydroxymethylimidazoles as starting materials and oxidizing these with a reagent containing a heavy metal, for example manganese dioxide, or with nitric acid. For the reagent oxidation method mentioned above, EP 0 514 198 A1 (under the heading "Intermediate 67") may be cited and, for the nitric acid oxidation method USP 4 107 308 for instance.

However, the method comprising oxidizing hydroxymethylimidazoles with a heavy metal reagent such as manganese dioxide is disadvantageous in that much labor is required for heavy metal handling or waste catalyst treatment and disposal. The method comprising oxidizing hydroxymethylimidazoles with nitric acid is very disadvantageous for commercial scale operation because of the low yield of the desired products and the generation of nitrogen oxides, among others.

OBJECT OF THE INVENTION

Accordingly, it is an object of the present invention to provide, under these circumstance, a commercially advantageous method of producing formylimidazoles in high yields using hydroxymethylimidazoles as the starting materials without encountering any substantial difficulty in handling.

SUMMARY OF THE INVENTION

The method of the invention for producing formylimidazoles is characterized in that, in producing formylimidazoles by catalytically oxidizing hydroxymethylimidazoles having the hydroxymethyl group either at position 4 or at position 5, the catalytic oxidation is carried out in the presence of a noble metal catalyst while blowing oxygen or air into the system.

In that case, it is particularly desirable for attaining better yield that the catalytic oxidation in the presence of a noble metal catalyst should be carried out in a solvent comprising an aqueous alkali or a mixed solvent composed of an aqueous alkali and an organic solvent immiscible with water.

In the following, the invention is described in further detail.

DETAILED DESCRIPTION OF THE INVENTION

In accordance with the present invention, formylimidazoles are produced by subjecting hydroxymethylimidazoles having the hydroxymethyl group either at position 4 or at position 5 to catalytic oxidation. The catalytic oxidation reaction may be represented by the following reaction formula (1) or (2).

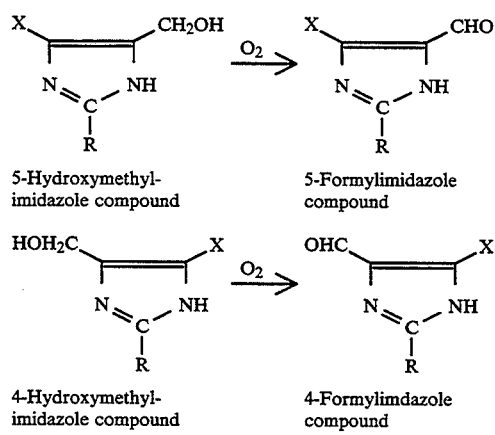

5-Hydroxymethyl-imidazole compound → 5-Formylimidazole compound

4-Hydroxymethyl-imidazole compound → 4-Formylimdazole compound

In the above formulas, R is a hydrogen atom or an alkyl group containing 1 to 5 carbon atoms, in particular a n-butyl group. X is a hydrogen atom, a halogen atom such as a chlorine or bromine atom, or an unsubstituted or substituted alkyl group containing 1 to 12 carbon atoms. The hydrogen atom of the imidazole ring NH may be substituted by an unsubstituted or substituted alkyl group containing 1 to 12 carbon atoms. The starting materials, namely 4- or 5-hydroxymethylimidazoles, include, as typical examples, the following:

5-Hydroxymethylimidazole,
4-Methyl-5-hydroxymethylimidazole,
2-Methyl-5-hydroxymethylimidazole,
2-Propyl-5-hydroxymethylimidazole,
2-Butyl-5-hydroxymethylimidazole,
2-Propyl-4-chloro-5-hydroxymethylimidazole,
2-Butyl-4-chloro-5-hydroxymethylimidazole and the like 5-hydroxymethylimidazoles and the corresponding 4-hydroxymethylimidazoles derived from such 5-hydroxymethylimidazoles by interchanging the positions 4 and 5.

In accordance with the invention, the above catalytic oxidation is conducted in the presence of a noble metal catalyst. As the noble metal catalyst, there may be mentioned a noble metal (inclusive of the metallic form as well as the form of a salt, oxide or the like) selected from the group consisting of platinum, palladium and gold. In particular, platinum and palladium are suited for practical use. These noble metals may be used in combination with bismuth, cerium, lead, indium or the like as a second component.

The noble metal catalyst is used as such or, when necessary, in the form supported on a carrier such as active carbon, silica or alumina.

The catalytic oxidation in the presence of such a noble metal catalyst is carried out in an appropriate solvent. Generally, the solvent is used in an amount of 3 to 50 parts by weight per part by weight of the starting material.

The solvent to be used includes, among others, lower carboxylic acids (e.g. acetic acid, propionic acid, etc.) or aqueous lower carboxylic acids, alcohols (e.g. tert-butanol etc.) or aqueous alcohols, ketones (e.g. acetone, methyl ethyl ketone, etc.) or aqueous ketones, ethers (e.g. dioxane, tetrahydrofuran, etc.) or aqueous ethers, and carboxylic acid esters (e.g. methyl acetate, ethyl acetate, etc.) or aqueous carboxylic acid esters. It is advantageous to use aqueous (water-containing) solvents from the product yield viewpoint in the case of lower carboxylic acids and from the product recovery viewpoint in the case of other solvents. In this case, it is practical that the water content be 1 to 70% by weight, preferably 10 to 60% by weight. Hereinafter, these solvents are referred to as "group 1 solvents."

For achieving further improved product yield, it is particularly desirable that the catalytic oxidation in the presence of the noble metal catalyst mentioned above should be performed in an aqueous alkali (i). It is also desirable that said oxidation should be carried out in a mixed solvent (ii) composed of an aqueous alkali and an organic solvent immiscible with water. Hereinafter, solvents of the type (i) are referred to as "group 2 solvents" and solvents of the type (ii) as "group 3 solvents."

As the alkali to be used in the group 2 and group 3 solvents, there may be mentioned sodium hydroxide, potassium hydroxide, sodium carbonate, potassium carbonate and sodium acetate, among others.

As the organic solvent immiscible with water in the group 3 solvents, there may be mentioned ketones, such as methyl isobutyl ketone etc., esters, such as ethyl acetate etc., halogenated hydrocarbons, such as ethylene dichloride etc., aromatic hydrocarbons, such as toluene etc., and aliphatic hydrocarbons, such as cyclohexane etc., among others. These organic solvents may be used either singly or in combination as a mixture of two or more of them.

From the practical use viewpoint, the proportions of the organic solvent immiscible with water and the aqueous alkali in the group 3 solvents are within the range of 1:100 to 100:1, preferably 10:1 to 1:10.

When an aqueous alkali (group 2 solvent) is used as the solvent, the alkali should be used in an amount of not less than 0.9 mole, preferably 1.0 to 1.5 moles, per mole of the starting material hydroxymethylimidazole. If the amount of the alkali is less than 0.9 mole, the product formylimidazole will not be dissolved in the system.

When a mixed solvent (type 3 solvent) composed of an organic solvent immiscible with water and an aqueous alkali is used as the solvent, the alkali is used desirably in an amount of not less than 0.01 mole, preferably 0.05 to 1.5 mole, per mole of the starting material hydroxymethyl imidazole.

When group 1 solvents are used, the catalyst is used suitably in an amount of 0.1 to 50 mole percent, preferably 1 to 20 mole percent, on the noble metal basis, per mole of the starting material hydroxymethylimidazole.

When group 2 or group 3 solvents are used, the catalyst is used suitably in an amount of 0.01 to 50 mole percent, preferably 0.1 to 20 mole percent, on the noble metal basis, per mole of the starting material hydroxymethylimidazole.

In carrying out the catalytic oxidation, the reactor is charged with one of the solvents mentioned above, and the catalyst and the starting material hydroxymethylimidazole are fed to the reactor.

Each component can be fed in a manner arbitrarily selected, for example all at once, portionwise, continuously or dropwise. Generally, each component is fed all at once.

When a group 1 solvent is used as the solvent, the reaction temperature is suitably not lower than 50° C., preferably 60° to 170° C., and the reaction time is suitably within the range of 3 to 24 hours, preferably 5 to 15 hours.

When a group 2 or group 3 solvent is used as the solvent, the reaction temperature may be within the range of 0° C. to the refluxing temperature but is suitably not lower than room temperature, preferably 20° to 80° C., and the reaction time is suitably within the range of 1 to 24 hours, preferably 2 to 15 hours.

For effecting the catalytic oxidation reaction, oxygen or air is introduced into the reaction system. The system may be under atmospheric pressure or under increased pressure. Introduction of oxygen or air is carried out at a rate of about 0.001 to 1.0 liters per minute per liter of the liquid reaction mixture. When no more oxygen absorption is observable, the reaction is discontinued and the catalyst is removed from the reaction mixture by filtration.

When a group 1 solvent is used, the filtrate is concentrated under reduced pressure and crystals of the desired formylimidazole are collected and, if necessary, subjected to further purification.

When a group 2 solvent is used, the product formylimidazole is found dissolved in the filtrate in the form of a salt and, therefore, the filtrate is neutralized with an inorganic acid, such as sulfuric acid or hydrochloric acid, and crystals of the product formylimidazole are collected and, if necessary, subjected to further purification.

When a group 3 solvent is used, the filtrate is neutralized with an acid and then allowed to separate into two layers, the aqueous layer is separated, the organic layer is concentrated under reduced pressure and crystals of the product formylimidazole are collected and, if necessary, subjected to further purification.

The yield of the desired product is not less than 60% when group 1 solvents are used and, when group 2 or group 3 solvents are used, it is not less than 90%, based on the starting material hydroxymethylimidazole.

The method of the invention makes it possible to obtain the desired formylimidazoles, which are useful as raw materials in the production of drugs such as diuretics and antihypertensive agents, in high yields by the catalytic oxidation method by using a noble metal catalyst, which is easy to handle on an industrial scale and further by using a specific solvent. Therefore, the method of the invention is very advantageous from the economical and commercial production viewpoints.

EXAMPLE

The following examples are further illustrative of the present invention. In Examples 1 to 7, mixed solvents composed of an organic solvent immiscible with water and an aqueous alkali (group 3 solvents) were used as the solvents. In Examples 8 to 13, solvents comprising an aqueous alkali (group 2 solvents) were used as the solvents. In Examples 14 to 19, aqueous solvents (group 1 solvents) were used as the solvents.

EXAMPLE 1

2-n-Butyl-4-chloro-5-hydroxymethylimidazole (11.4 g, 60 millimoles) was dissolved in 210 ml of methyl isobutyl ketone, and 30 ml of an aqueous alkali with 0.24 g (6 millimoles) of sodium hydroxide dissolved therein was added to the solution. After further addition of 4.8 g of a platinum-bismuth catalyst (5% platinum and 2% bismuth supported on active carbon; water content 50%) (the quantity of platinum used being 0.6 millimole), the temperature of the system was raised to 75° C. and catalytic oxidation was carried out by blowing oxygen into the mixture at a rate of 80 ml/minute for 4 hours with stirring.

After completion of the reaction, the catalyst was filtered off from the reaction mixture, and the filtrate was neutralized with diluted sulfuric acid (pH of the aqueous layer: 7) and then allowed to separate into two layers. The aqueous layer was separated and the organic layer was concentrated under reduced pressure at 50° C. to give light-yellow crystals in 95% yield. Infrared spectroscopy and nuclear magnetic resonance (NMR) spectrometry verified that the crystalline product was 2-n-butyl-4-chloro-5-formylimidazole.

EXAMPLE 2

The procedure of Example 1 was followed except that potassium hydroxide was used in lieu of sodium hydroxide and the reaction was carried out at 77° C. for 5 hours, whereupon 2-n-butyl-4-chloro-5-formylimidazole was obtained in 94% yield.

EXAMPLE 3

The procedure of Example 1 was followed except that ethylene dichloride was used in lieu of the solvent methyl isobutyl ketone, whereupon 2-n-butyl-4-chloro-5-formylimidazole was obtained in 88% yield.

EXAMPLE 4

The procedure of Example 1 was followed except that toluene was used in lieu of the solvent methyl isobutyl ketone, whereupon 2-n-butyl-4-chloro-5-formylimidazole was obtained in 90% yield.

EXAMPLE 5

2-n-Butyl-5-hydroxymethylimidazole (18.5 g, 120 millimolles) was dissolved in 210 ml of methyl isobutyl ketone, and 30 ml of an aqueous alkali with 0.48 g (12 millimoles) of sodium hydroxide dissolved therein was added to the solution. After further addition of 2.4 g of a platinum-bismuth catalyst (5% platinum and 2% bismuth supported on active carbon; water content 50%) (the quantity of platinum used being 0.3 millimole), the temperature was raised to 80° C. and catalytic oxidation was effected by blowing oxygen into the mixture at a rate of 80 ml/minute for 5 hours with stirring.

After completion of the reaction, the catalyst was filtered off from the reaction mixture, and the filtrate was neutralized with diluted sulfuric acid and then allowed to separate into two layers. The aqueous layer was separated and the organic layer was concentrated under reduced pressure at 50° C. to give light-yellow crystals in 93% yield. Infrared spectroscopy and NMR spectrometry verified that the crystalline product was 2-n-butyl-5-formylimidazole.

EXAMPLE 6

Catalytic oxidation was carried out following the procedure of Example 5 except that 2.4 g of platinum black (the quantity of platinum black used being 12.3 millimoles) was used as the catalyst. Infrared spectroscopy and NMR spectrometry verified that the product obtained was 2-n-butyl-5-formylimidazole. The yield was 91%.

EXAMPLE 7

The procedure of Example 1 was repeated except that 4-methyl-5-hydroxymethylimidazole was used as the starting material. Infrared spectroscopy and NMR spectrometry verified that the product obtained was 4-methyl-5-formylimidazole. The yield was 82%.

EXAMPLE 8

2-n-Butyl-4-chloro-5-hydroxymethylimidazole (20.0 g, 105 millimoles) was suspended in 200 ml of an aqueous alkali containing 5.1 g (128 millimoles) of sodium hydroxide dissolved therein and, after further addition of 5.4 g of a platinum-bismuth catalyst (5% platinum and 2% bismuth supported on active carbon; water content 50%) (the quantity of platinum used being 0.7 millimole), catalytic oxidation was carried out by blowing oxygen into the mixture at a rate of 80 ml/minute for 2.5 hours with stirring at room temperature (21°–26° C.).

After completion of the reaction, the catalyst was filtered off from the reaction mixture, and the filtrate was neutralized with 20% sulfuric acid to give light-yellow crystals in 95% yield. Infrared spectroscopy and NMR spectrometry verified that the crystalline product was 2-n-butyl-4-chloro-5-formylimidazole.

EXAMPLE 9

The procedure of Example 8 was repeated except that potassium hydroxide was used in lieu of sodium hydroxide. 2-n-Butyl-4-chloro-5-formylimidazole was obtained in 94% yield.

EXAMPLE 10

The procedure of Example 8 was repeated except that potassium carbonate was used in lieu of sodium hydroxide. 2-n-Butyl-4-chloro-5-formylimidazole was obtained in 83% yield.

EXAMPLE 11

2-n-Butyl-5-hydroxymethylimidazole (7.5 g, 48 millimoles) was suspended in 200 ml of an aqueous alkali containing 2.0 g (50 millimoles) of sodium hydroxide and, after further addition of 2.0 g of a platinum-bismuth catalyst (5% platinum and 2% bismuth supported on active carbon; water content 50%) (the quantity of platinum used being 0.26 millimole), catalytic oxidation was carried out by blowing oxygen into the mixture at a rate of 80 ml/minute with stirring at room temperature for 6 hours and then at 65° C. for 2 hours.

After completion of the reaction, the catalyst was filtered off from the reaction mixture, and the filtrate was neutralized with 20% sulfuric acid to give light-yellow crystals in 91% yield. Infrared spectroscopy and NMR spectrometry verified that the crystalline product was 2-n-butyl-5-formylimidazole.

EXAMPLE 12

The procedure of Example 11 was repeated except that 1.0 g of platinum black (the quantity of platinum black used being 5.1 millimoles) was used as the catalyst. Infrared spectroscopy and NMR spectrometry verified that the product obtained was 2-n-butyl-5-formylimidazole. The yield was 92%.

EXAMPLE 13

The procedure of Example 8 was repeated except that 4-methyl-5-hydroxymethylimidazole was used as the starting material. Infrared spectroscopy and NMR spectrometry verified that the product obtained was 4-methyl-5-formylimidazole. The yield was 83%.

EXAMPLE 14

2-n-Butyl-5-hydroxymethylimidazole (7.7 g, 50 millimoles) was dissolved in 210 ml of a 25% solution of tert-butanol in water and, after addition of 1 g of platinum black (the quantity of platinum black used being 5.1 millimoles), the temperature of the system was raised to 77° C. and catalytic oxidation was effected by blowing oxygen into the system at a rate of 200 ml/minute for 6 hours with stirring.

After completion of the reaction, the catalyst was filtered off from the reaction mixture, and the filtrate was concentrated under reduced pressure at 50° C. to give 7.8 g (0.046 mole) of light-yellow crystals. Gas chromatographic analysis revealed that the crystalline product had a purity of 90% and the yield was 92%. Infrared spectroscopy and NMT spectrometry verified that the crystalline product was 2-n-butyl-5-formylimidazole.

EXAMPLE 15

The procedure of Example 14 was followed except that a 50% aqueous solution of acetic acid was used as the solvent and the reaction temperature was raised to 95° C., whereupon 2-n-butyl-5-formylimidazole was obtained in 68% yield.

EXAMPLE 16

The procedure of Example 14 was followed except that a 30% solution of tert-butanol in water was used as the solvent and 5.0 g of platinum on active carbon (10% by weight of platinum supported) (the quantity of platinum used being 2.56 millimoles) as the catalyst. 2-n-Butyl-5-formylimidazole was obtained in 72% yield.

EXAMPLE 17

The procedure of Example 14 was followed except that a 25% solution of tert-butanol in water was used as the solvent and 5.0 g of palladium on active carbon (10% by weight of palladium supported) (the quantity of palladium used being 4.7 millimoles) as the catalyst. 2-n-Butyl-5-formylimidazole was obtained in 60% yield.

EXAMPLE 18

2-n-Butyl-4-chloro-5-hydroxymethylimidazole (3.8 g, 20 millimoles) was dissolved in 200 ml of a 25% solution of tert-butanol in water and, after addition of 0.4 g of platinum black (the quantity of platinum black used being 2.05 millimoles), the temperature was raised to 77° C. and catalytic oxidation was carried out by blowing oxygen into the mixture at a rate of 200 ml/minute for 6 hours with stirring.

After completion of the reaction, the catalyst was filtered off from the reaction mixture, and the filtrate was cooled to cause precipitation of crystals. The crystals were collected by filtration and dried, whereupon 2.8 g of a light-yellow crystalline product was obtained. Liquid chromatographic purity analysis revealed that the crystalline product had a purity of 98% and the yield was 74%. Infrared spectroscopy and NMR spectrometry verified that the crystalline product was 2-n-butyl-4-chloro-5-formylimidazole.

EXAMPLE 19

Using 3.5 g (20 millimoles) of 2-n-propyl-4-chloro-5-hydroxymethylimidazole in lieu of 2-n-butyl-4-chloro-5-hydroxymethylimidazole, the procedure of Example 18 was followed for catalytic oxidation.

After completion of the reaction, the catalyst was filtered off from the reaction mixture, and the filtrate was concentrated under reduced pressure to about 5 ml, whereupon crystals precipitated out. The crystals were collected by filtration and dried. Thus was obtained 2.5 g of a light-yellow crystalline product. Liquid chromatographic purity analysis revealed that the crystalline product had a purity of 97% and the yield was 69%. Infrared spectroscopy and NMR spectrometry verified that said product was 2-n-propyl-4-chloro-5-formylimidazole.

What is claimed is:

1. A method of producing formylimidazoles by catalytic oxidation of a 4- or 5-hydroxymethylimidazole compound which comprises effecting the catalytic oxidation by blowing oxygen or air into the reaction system in the presence of a noble metal catalyst.

2. The method of claim 1, wherein the noble metal catalyst is a platinum or palladium catalyst.

3. The method of claim 1, wherein the catalytic oxidation in the presence of a noble metal catalyst is carried out in a solvent comprising an aqueous alkali.

4. The method of claim 1, wherein the catalytic oxidation in the presence of a noble metal catalyst is carried out in a mixed solvent composed of an aqueous alkali and an organic solvent immiscible with water.

5. The method of claim 4, wherein the organic solvent immiscible with water is methyl isobutyl ketone.

* * * * *